(12) United States Patent
Rustum et al.

(10) Patent No.: US 7,534,818 B1
(45) Date of Patent: May 19, 2009

(54) METHOD OF REDUCING ALOPECIA AND BLADDER TOXICITY OF CYCLOPHOSPHAMIDE

(75) Inventors: Youcef M. Rustum, Amherst, NY (US); Shousong Cao, East Amherst, NY (US); Farukh Durrani, Snyder, NY (US); Karoly Toth, North Amherst, NY (US); Peter Kanter, East Aurora, NY (US); Harry Slocum, Kenmore, NY (US)

(73) Assignee: Health Research, Inc., Buffalo, NY (US)

( * ) Notice: Subject to any disclaimer, the term of this patent is extended or adjusted under 35 U.S.C. 154(b) by 494 days.

(21) Appl. No.: 10/663,109

(22) Filed: Sep. 15, 2003

(51) Int. Cl.
*A01N 59/02* (2006.01)
(52) U.S. Cl. ...................... 514/561; 514/706
(58) Field of Classification Search ................ 514/706, 514/99, 110, 561
See application file for complete search history.

(56) References Cited

U.S. PATENT DOCUMENTS

| 4,564,634 | A | | 1/1986 | Revici |
| 4,617,189 | A | | 10/1986 | Stockel et al. |
| 5,001,051 | A | * | 3/1991 | Miller et al. ............... 435/6 |
| 5,262,149 | A | * | 11/1993 | Sredni et al. .............. 424/650 |
| 5,552,440 | A | | 9/1996 | Crooks et al. |
| 6,090,414 | A | | 7/2000 | Passwater et al. |
| 6,197,295 | B1 | | 3/2001 | Hsia et al. |
| 6,939,893 | B2 | * | 9/2005 | Rustum et al. ............. 514/561 |
| 2001/0044431 | A1 | | 11/2001 | Rodriguez |
| 2004/0197430 | A1 | | 10/2004 | Meyrowitz |
| 2005/0026852 | A1 | * | 2/2005 | Rustum et al. ............. 514/34 |
| 2005/0197399 | A1 | * | 9/2005 | Fakih et al. ............... 514/561 |

FOREIGN PATENT DOCUMENTS

WO    WO 99/64018    12/1999
WO    WO 00/67762    11/2000

OTHER PUBLICATIONS

Boucher et al., *Oral Selenium Supplementation in Rats Reduces Cardiac Toxicity of Adriamycin During Ischemia and Reperfusion*, Nutrition, Sep.-Oct. 1995, vol. 11 (5 Suppl.), pp. 708-711.
Dong et al., *Identification of Molecular Targets Associated with Selenium-Induced Growth Inhibition in Human Breast Cells Using cDNA Microarrays*, Cancer Research, Feb. 1, 2002, vol. 62, pp. 708-714.
El-Bayoumy et al., *The Protective Role of Selenium on Genetic Damage and on Cancer*, Mutation Research, 2001, vol. 475, pp. 123-139.
Frenkel et al., *A Prevention Strategy for Circumventing Drug Resistance in Cancer Chemotherapy*, Current Pharmaceutical Design, 2001, vol. 7, pp. 1595-1614.
Hu et al., *The Protective Role of Selenium on the Toxicity of Cisplatin-Contained Chemotherapy Regimen in Cancer Patients*, Biological Trace Element Research, 1997, vol. 56, pp. 331-341.
Kajander et al., *Effects of Selenomethionine Metabolism in Cultured Malignant Cells*, Biochem. J., 1990, vol. 267, pp. 767-774.
Ohkawa et al., *The Effects of Co-Administration of Selenium and Cis-platin (CDDP) on CDDP-Induced Toxicity and Antitumor Activity*, Br. J. Cancer, 1988, vol. 58, pp. 34-41.
Seija K., *Protective Role of Selenium Against the Toxicity of Multi-Drug Chemotherapy in Patients with Ovarian Cancer*, , Pharmazie, 2000, vol. 55, No. 12, pp. 958-959.
Seo et al., *Selenomethionine Regulation of p53 by a Refl-Dependent Redox Mechanism*, PNAS, Oct. 29, 2002, vol. 99, No. 22, pp. 14548-14553.
Wang et al., *Induction of Caspase-Mediated Apoptosis and Cell-Cycle $G_1$ Arrest by Selenium Metabolite Methylselenol*, Molecular Carcinogenesis, 2002, vol. 34, pp. 113-120.
Konorev, et. al., *Cell-Permeable Superoxide Dismutase and Glutathione Peroxidase Mimetics Afford Superior Protection Against Doxorubicin-Induced Cardiotoxicity: The Role of Reactive Oxygen and Nitrogen Intermediates*, Archives Biochem. Biophysics, 1999, 368 (2), pp. 421-428, abstract.
Korac, et al., *Doxorubicin, Toxicity to the Skin: Possibility of Protection With Antioxidants Enriched Yeast*, J. Dermat. Sci., 2001, 25 (1) pp. 45-52, abstract.
Chen, et al., *Protective Effects of Selenium Supplementation in Minimizing 5-Glorouracil Induced Lipid Peroxidative Damage of the Small Intestine*, J. Trace Elements in Experimental Med., 1997, 10 (3), p. 163-171.
Vadgama J. et al., *Effect of Selenium in Combination With Adriamycin or Taxol on Several Different Cancer Cells*, Anticancer Research 20:1391-1414, 2000.

\* cited by examiner

*Primary Examiner*—Frederick Krass
*Assistant Examiner*—Chris E Simmons
(74) *Attorney, Agent, or Firm*—Hodgson Russ LLP

(57) ABSTRACT

The present invention discloses a method for reducing alopecia and bladder toxicity associated with the anti-cancer agent cyclophosphamide. The method comprises administering to an individual, in need of such a treatment, cyclophosphamide and a selenium compound. The selenium compounds may be administered before, during or after administration of the anti-cancer agent.

1 Claim, 4 Drawing Sheets

METHOD OF REDUCING ALOPECIA AND BLADDER TOXICITY OF CYCLOPHOSPHAMIDE

FIELD OF THE INVENTION

This invention relates generally to the field of cancer therapy and more particularly to a method for reducing toxicity of cyclophosphamide.

DESCRIPTION OF RELATED ART

Chemotherapy is now a recognized and widely used modality of cancer treatment. Depending upon the type of cancer, chemotherapy is often the primary course of treatment. For example, chemotherapy is widely used either alone or in combination with other treatments such as radiation treatment for a variety of cancers including cancer of the ovary, testis, breast, bladder, colon, head and neck as well as leukemia, lymphomas, sarcomas, melanomas, myelomas and others.

Chemotherapeutic agents are broadly classified into a number of groups. The majority of anticancer drugs act as cytotoxic drugs. The classification of these drugs into groups is mechanism based. While chemotherapeutic agents have proven extremely useful in the treatment of cancer, nearly all of them are associated with significant toxic effects because of their potential to kill cancerous as well as healthy cells. For example, organ-specific toxicity is associated with clinically active chemotherapeutic agents and represents challenging health problems.

Alopecia and bladder dysfunction are reported to be toxicity effects of some chemotherapy treatments. Cyclophosphamide is an example of a chemotherapeutic agent used for the treatment of breast, lung and ovarian cancers and known to be associated with alopecia and bladder toxicity affecting as many as 20-30% of treated patients. Chemotherapy induced alopecia is one of the most distressing aspects of cancer chemotherapy. In addition to Cyclophosphamide, doxorubicin, taxanes and vincristine also generally cause the most profound alopecia. Scalp-cooling devices to treat alopecia have been employed with mixed results (Seipp et al., In Cancer Principles and Practice of Oncology, Ed. VT DeVita (5th Ed.), p 2757, 1997; Protiere et al., 2002, Support Care Cancer, 10(7):529-537). Bladder toxicity is also most common toxicity in terms of hemorrhagic cystitis (Levine et al, 1989, J. Urol., 141:1063; Watson et al., 1973, Br. J. Urol., 45:606; Droller et al., 1982, 20:256; Walther et al., 1997, In Cancer Principles and Practice of Oncology, Ed. VT DeVita (5th Ed.), p 2725-2726.

Toxicity associated with anticancer drugs often forces discontinuation of treatment which may negatively impact the prognosis of a patient's condition and clinical outcome and result in compromising the quality of life. These toxicities are clinically managed by drug dose reduction or delay of treatment. Previous attempts to reduce chemotherapy associated alopecia, such as by using cold caps, have met with limited success (Protiere et al., 2002, Support Care Cancer, 10(7): 529-537).

Some studies attempting to address the issue of the effect of selenium on toxicity of anticancer agents in vitro have yielded conflicting results (Steifel et al., 1999, WO 99/64018; Chen et al., 1986, J. Nurtition, 116(12):2453-2465; Dobric et al., 1998, J. Environ. Pathol. Toxicol Oncol., 17:291-299; Van Vleet et al., 1980, Am. J. Pathol., 99:13-42; Van Vleet et al., Am. J. Vet Res., 1980, 41(5):691-699; Van Vleet et al., Am. J. Vet Res., 1981, 42(7):1153-1159). Given the inherent difficulties of extrapolating the in vitro studies to treatment regimens for cancer patients, the toxicity of anticancer agents such as cyclophosphamide, continues to pose a problem for the use of these chemotherapeutic agents. Accordingly, it would be beneficial to develop new approaches that can selectively prevent the toxic side effects of cyclophosphamide with the potential for increase in therapeutic efficacy.

SUMMARY OF THE INVENTION

In the present invention it was observed that administration of selenium compounds reduces toxicity associated with administration of cyclophosphamide. Cyclophosphamide induced toxicity includes weight loss, alopecia and bladder toxicity. Data is presented for in vivo studies using an animal model.

Accordingly, the present invention discloses a method for reducing toxicity of cyclophosphamide including alopecia and bladder toxicity. The method comprises administering to an individual, in need of treatment, cyclophosphamide and a selenium compound. The selenium compounds may be administered before, during or after administration of the anti-cancer agent. In one embodiment, the selenium compound is administered prior to chemotherapy and may be continued during and after the chemotherapy.

BRIEF DESCRIPTION OF THE FIGURES

FIG. 4 show 2 rats for each group and FIG. 5 shows a magnified view of 1 rat for each group from FIG. 4.

DETAILED DESCRIPTION OF THE INVENTION

Figure 1:
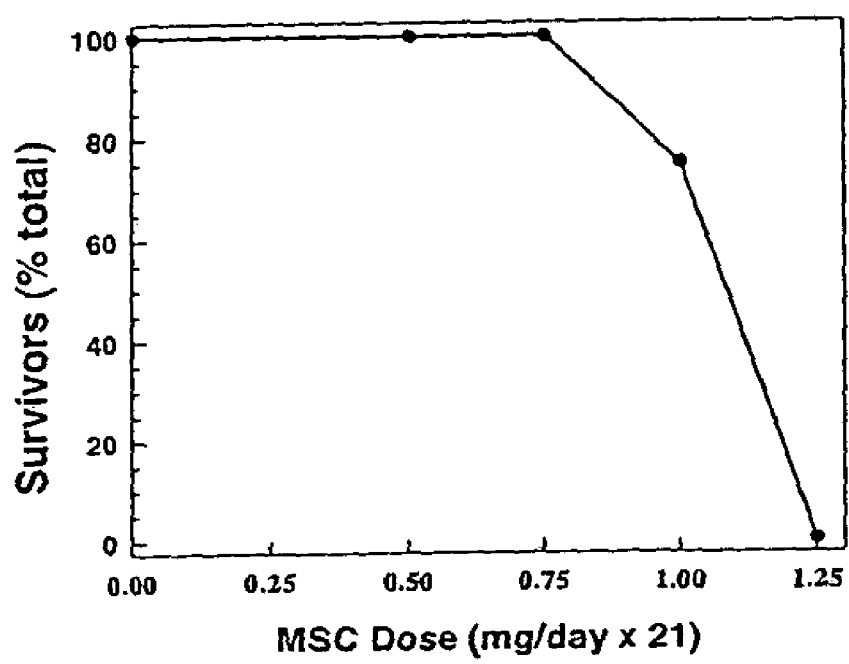
FIG. 1 is a representation of the dose response curve for the effect of 5-methylselenocysteine (MSC) on the survival of normal rats.

The term "therapeutic dose" as used herein means the dosage of a therapeutic agent that is acceptable for use clinically with respect to its toxicity without the co-administration of selenium compounds.

The term "bladder toxicity" as used herein means a finding of bloody urine, hematuria or hemorrhagic cystitis.

The present invention discloses a method for reducing the toxicity of cyclophosphamide while maintaining or enhancing its efficacy. The method comprises administering to an individual, in need of such a treatment, cyclophosphamide and one or more selenium compounds. The selenium compounds may be administered before, during or after administration of cyclophosphamide. By combining chemotherapy with the administration of selenium compounds, some of the side effects of cyclophosphamide such as weight loss, alopecia and bladder toxicity can be decreased.

Selenium compounds useful for the present invention can be from either organic or inorganic forms. It is preferable to use selenium from organic forms since these are known to be less toxic. Examples of useful selenium compounds from organic forms include methylselenocysteine (MSC) and seleno-L-methionine (SLM). The doses of selenium compounds are in the range of about 200 µg/person to about 3.6 mg/person and maybe administered daily for 1 year or longer. It has been reported that up to 800 µg/patient is generally considered to be safe without associated toxicity.

The present invention comprises the steps of combining chemotherapy with the administration of selenium. Cyclophosphamide may be administered alone or combined with other chemotherapeutic agents accordingly to the criteria well known in the art of cancer chemotherapeutics. The dosage and administrative regimens of the cyclophosphamide are well within the purview of those skilled in the art. Selenium administration can be initiated before the start of chemotherapy, during chemotherapy or after cessation of chemotherapy. If initiated before the start of chemotherapy, selenium administration can be continued during the chemotherapy and after cessation of chemotherapy. Similarly, if initiated during chemotherapy, selenium administration can continue after cessation of chemotherapy.

To demonstrate the effect of selenium in reducing the toxic effect of cyclophosphamide, studies were carried out in normal rats. The results demonstrated that MSC, a selenium containing-compound is highly effective in preventing alopecia and severe bladder toxicity associated with cyclophosphamide. The results reported here in normal rats were generated with cyclophosphamide as an example of chemotherapeutic agents causing significant alopecia.

When selenium is administered to an individual in need of therapy for cancer to reduce the toxicity, the dose of the chemotherapeutic agent (or radiation dose) can be increased so as to have greater efficacy.

The following examples are provided below to illustrate the present invention. These examples are intended to be illustrative and are not to be construed as limiting in any way.

EXAMPLE 1

This example describes the identification of non-toxic doses for the use of selenium. To illustrate this embodiment, different groups of adult Fisher rats were administered various doses of selenium for 21 days and survival of rats was monitored. Each group had 6 rats and each exempt group was repeated 3-4 times. The results are shown in FIG. 1. The data indicate that up to 0.75 mg/rat/d×21 MSC is not toxic (less than 5% weight loss, no lethality). Toxicity was observed at higher doses with 75% and 0% of animals surviving treatment with 1 mg and 1.25 mg/kg MSC dose. Thus, for evaluation of the protective effect of MSC against chemotherapy induced toxicity, the dose and schedule of MSC used was 0.75 mg/rat/d up to 21 days orally.

EXAMPLE 2

This embodiment demonstrates that selenium reduces bladder toxicity induced by administration of cyclophosphamide. To illustrate this embodiment, the effect of cyclophosphamide administration was studied on rats in the presence or absence of selenium. Rats (Fisher rats) weighing 120-180 g were treated orally with 0.75 mg/rat/d MSC up to 21 days with the first dose administered fourteen (14) days prior to i.v. administration of cyclophosphamide. This dose and schedule of 5-Methylselenocysteine (MSC) was non-toxic yielding a weight loss of 7.4±2.4 (less than 10% of total body weight). Cyclophosphamide (Endoxan) was administered as a single i.v. push using 150 mg/kg×1. At four and twenty-four hrs post cyclophosphamide treatment, bladders were removed and examined histopathologically for tissue damage. Bladders were removed and fixed in formalin. Paraffin embedded sections were obtained and stained by hematoxylin-eosin staining by standard methods.

Figure 2:
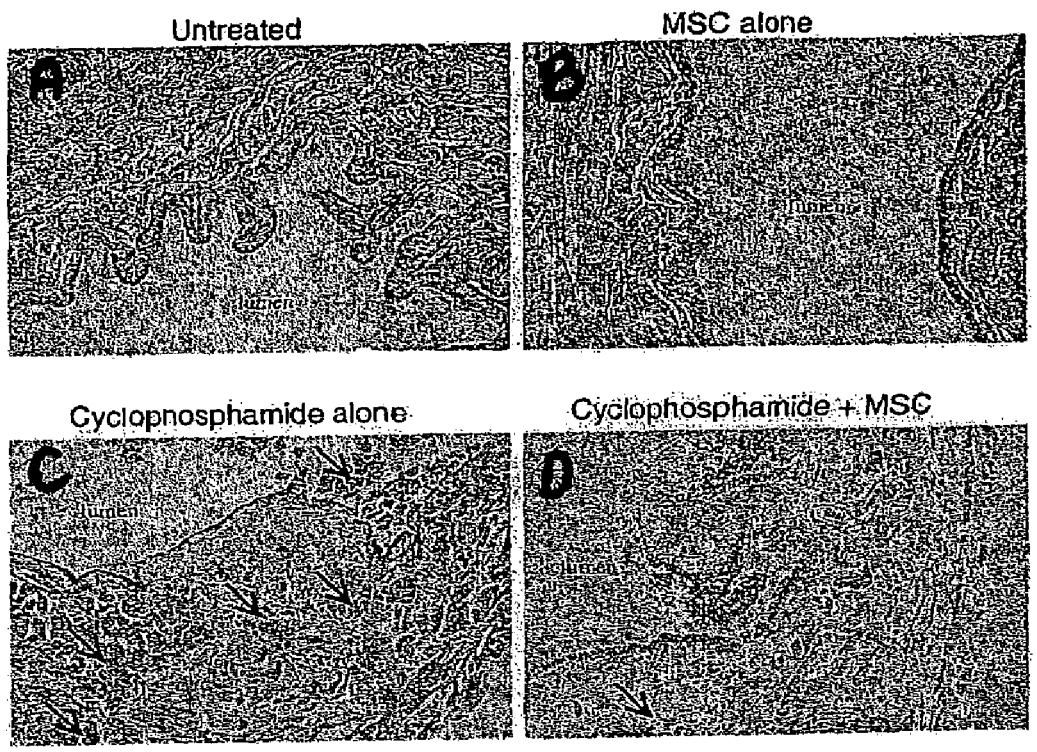
FIG. 2 is a representation of the effect of selenium compounds on the bladder toxicity of cyclophosphamide in rats. Cyclophosphamide was administered by a single intravenous (i.v.) push at 150 mg/kg. MSC was administered orally at 0.75 mg/kg/rat daily for 21 days with the first dose being given at 14 days before cyclophosphamide treatment. The animals were sacrificed 24 hours after cyclophosphamide treatment with or without MSC. Hemotoxylin eosin stained sections are shown for control (Panel A); MSC alone (Panel B); cyclphosphamide alone (Panel C) and cyclophosphamide plus MSC (Panel D).

The results are shown in FIG. 2. This figure shows photomicrographs of rat bladder 24 hrs after cyclosphosphamide treatment without and with MSC. Magnification for panels A and B is 100×, and for panels C and D is 200×. Panel A, shows the histologic picture of an untreated normal bladder. Panel B, demonstrates that there is no change after MSC treatment alone. Panel C, shows characteristic, severe hemorrhagic cystitis caused by cyclophosphamide alone. The hemorrhages (arrows) are destructive in the mucosa and in the bladder wall. Panel D, clearly shows the complete lack of hemorrhage after cyclophosphamide treatment combined with MSC, indicating the strong protective effect of MSC. Edema (arrow) is still present, but it is considered a minor lesion as compared to hemorrhage seen without MSC.

Figure 3:
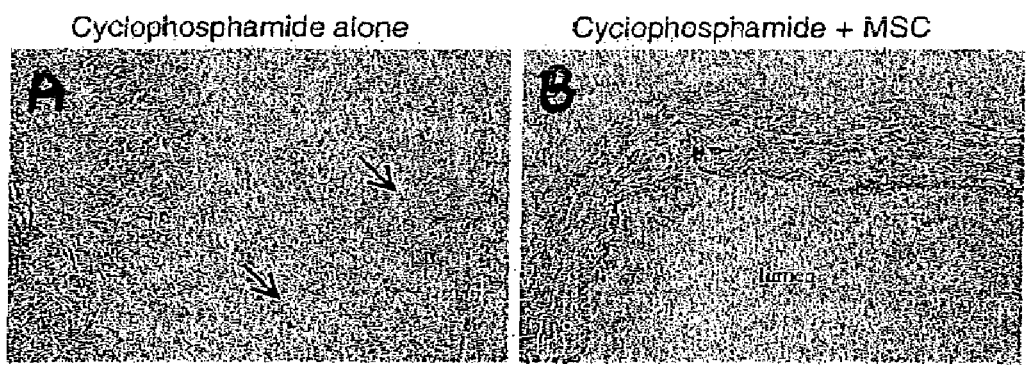
FIG. 3 is another representation of the effect of selenium on bladder toxicity of cyclophosphamide in rats. Hemotoxylin-eosin stained sections are shown for MSC alone (Panel A; 200×) and cyclophosphamide plus MSC (Panel B; 100×)

FIG. 3 is another representation of the protective effect of selenium on rat bladder. Panel A shows a section of the bladder 4 hrs after cyclophosphamide treatment. The section shows an acute mucosal edema (arrow) that is lacking in a corresponding section obtained from an animal in which MSC was coadministered with cyclophosphamide (Panel B). A long bladder segment seen in Panel B indicates preserved normal histological structure. Magnification for Panel A is 200×, and for Panel B is 100×. Edema occurred only in the cyclophosphamide treated group.

EXAMPLE 3

This embodiment demonstrates that selenium reduces alopecia induced by administration of cyclophosphamide. To illustrate this embodiment, the effect of cyclophosphamide administration was examined on rats in the presence or absence of selenium. Sections on the backs of rats (approximately 7 by 9 cm) were shaved and the animals randomized to treatment with MSC or vehicle before toxicity with cyclophosphamide. Cyclophosphamide (Endoxan) was administered as a single i.v. push using 100 mg/kg×1. MSC at 0.75 mg/rat/day was administered for twenty-one (21) days with the first dose administered fourteen (14) days prior to i.v.

administration of cyclophosphamide (100 mg/kg×1). Rats treated with cyclophosphamide alone and in combination with MSC were monitored for weight changes and alopecia at various times post therapy. Regrowth of hair was assessed at 30, 45 and 90 days post initiation of cyciophosphamide treatment.

Figure 4:
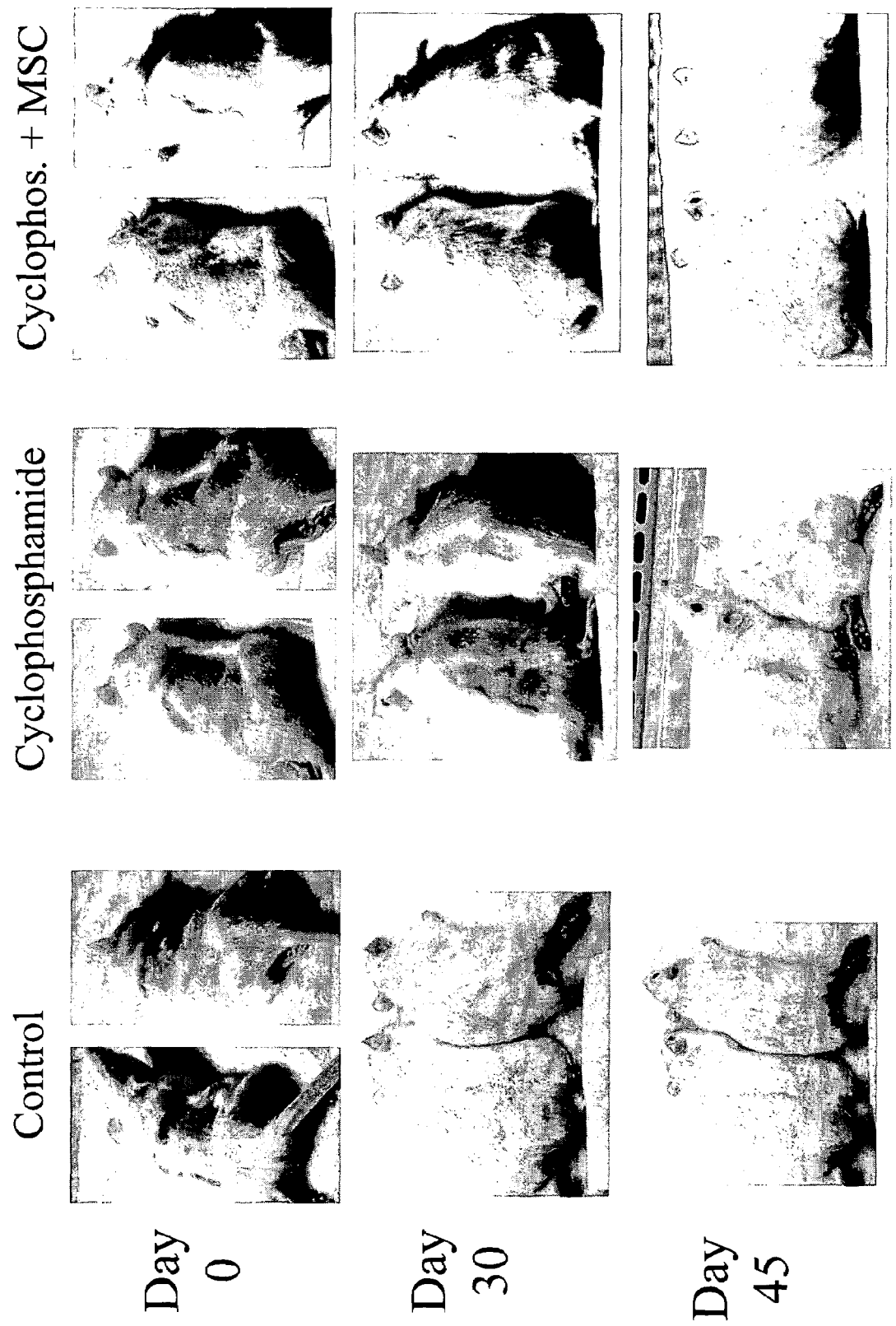
FIGS. 4 and 5 are representations of the effect of selenium on alopecia induced by cyclophosphamide in rats. The backs of rats were shaved and cyclophosphamide (100 mg/kg) was administered once by i.v. push and MSC was given p.o. daily for 21 days with the first dose being administered 14 days before cyclophosphamide treatment. Results are shown for control, cyclophosphamide and cyclophosphamide plus MSC treated rats at 0, 30 and 45 days after treatment.
Figure 5:
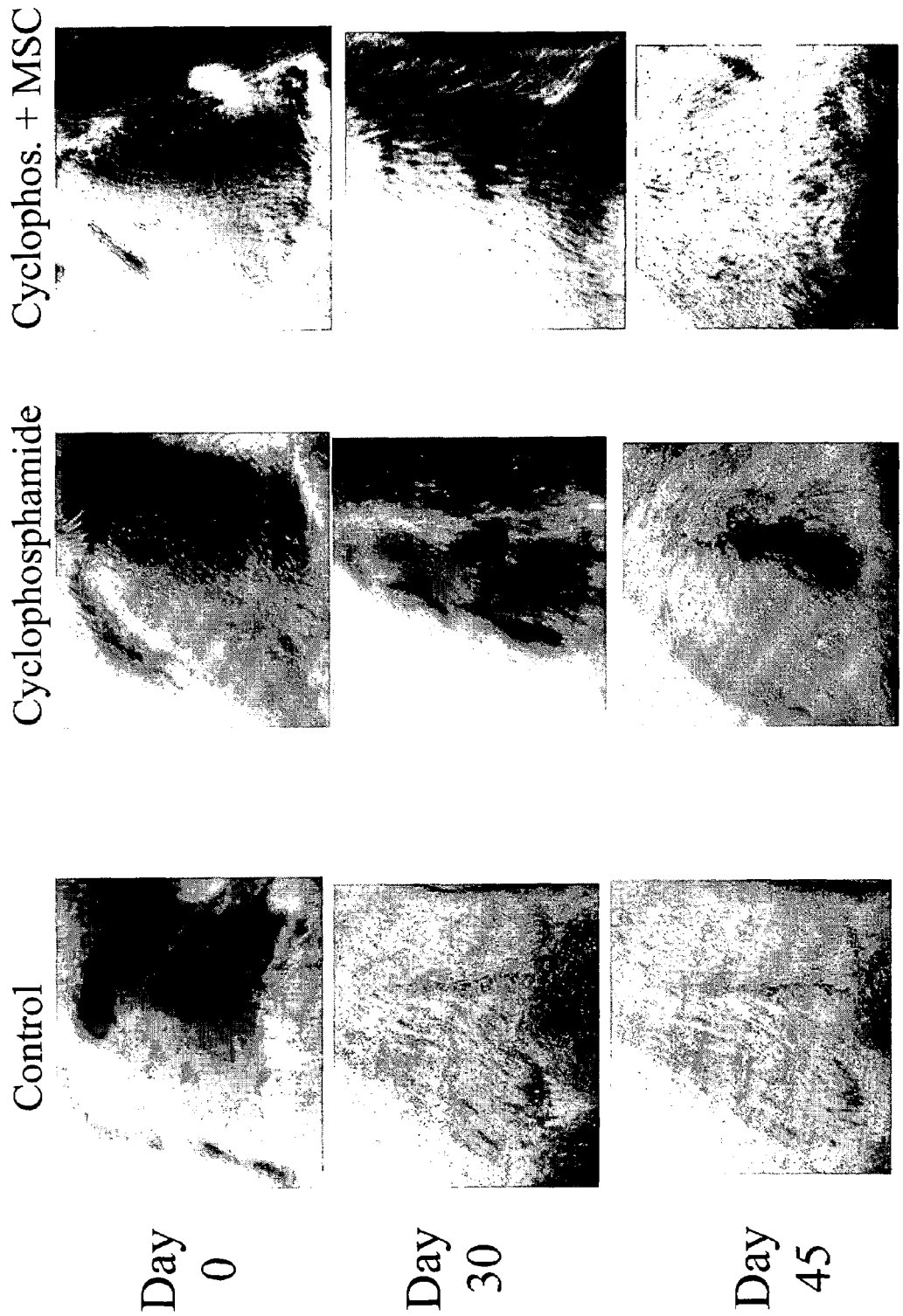

The effects of cyclophosphamide (100 mg/kg i.v.×1) alone and in combination with MSC (0.75 mg/rat/d×21) on alopecia in rats are shown in FIG. 4 for 1) untreated control; 2) treated rats with cyclophosophamide; and 3) treated rats with cyclophosphamide in combination with MSC. The results demonstrate recovery of regrowth of hair in control rats. For cyclophosphamide treated rats there was only partial recovery on days 30 and 45. However, when cyclophosphamide was administered in combination with MSC, the regrowth of hair was more than without MSC and was comparable to that of control rats. The data clearly demonstrated that MSC is effective in prevention of alopecia induced by cyclophosphamide. The weight loss observed with cyclophosphamide was also significantly reduced in rats treated with the combination.

EXAMPLE 4

This embodiment demonstrates that the protective effects of selenium are observed at concentrations at which the efficacy of the anti-tumor effect of the cyclophosphamide is not reduced and may even be enhanced. To determine whether the protective effects of MSC against toxicities induced by cyclophosphamide are selective, nude mice bearing human squamous cell carcinoma of head and neck tumor xenografts (A253 and FaDu) were treated with therapeutic doses of cyclophosphamide (100 mg/kg×1, i.v.) alone and in combination with MSC as described above. The results which are summarized in Table 1 indicate that MSC augments the anti-tumor activity of cyclophosphamide (cyclo.) in A253 and FaDu xenografts.

TABLE 1

| | Anti-tumor activity (% inhibition) | | | |
| --- | --- | --- | --- | --- |
| | A253 | | FaDu | |
| Treatment | Cyclo. | MSC + cyclo | Cyclo. | MSC + cyclo. |
| Tumor growth inhibition | 35% | 70% | 42% | 92% |

In summary, Selenium protects against cyclophosphamide induced toxocity including bladder toxicity (edema and telangiectasia and destructive hemorrhagic cystitis) and alopecia. Further, Selenium also increases the antitumor activity of cyclophosphamide.

The invention claimed is:

1. A method for reducing alopecia induced in an individual by the administration of cyclophosphamide in an amount of from 100 mg/kg to 150 mg/kg, the method comprising administering to the individual 0.75 mg/kg per day methylselenocysteine orally for 21 days, wherein the first dose of the methylselenocysteine is administered 14 days before the administration of the cyclophosphamide, wherein the alopecia induced by cyclophosphamide is less than the alopecia induced in the absence of methylselenocysteine.

* * * * *